United States Patent
Graham et al.

(10) Patent No.: US 11,977,217 B2
(45) Date of Patent: May 7, 2024

(54) INSERTION TOOL

(71) Applicants: General Electric Company, Schenectady, NY (US); Oliver Crispin Robotics Limited, Altrincham (GB)

(72) Inventors: Andrew Crispin Graham, Badminton (GB); Todd William Danko, Niskayuna, NY (US)

(73) Assignees: General Electric Company, Schenectady, NY (US); Oliver Crispin Robotics Limited, Altrincham (GB)

( * ) Notice: Subject to any disclaimer, the term of this patent is extended or adjusted under 35 U.S.C. 154(b) by 235 days.

(21) Appl. No.: 17/111,650

(22) Filed: Dec. 4, 2020

(65) Prior Publication Data
US 2022/0176524 A1  Jun. 9, 2022

(51) Int. Cl.
| | |
|---|---|
| G02B 23/24 | (2006.01) |
| B64F 5/40 | (2017.01) |
| F02C 7/00 | (2006.01) |
| G01N 21/88 | (2006.01) |
| G01N 21/954 | (2006.01) |

(52) U.S. Cl.
CPC .............. G02B 23/24 (2013.01); F02C 7/00 (2013.01); G01N 21/8803 (2013.01); G01N 21/954 (2013.01); G02B 23/2476 (2013.01); B64F 5/40 (2017.01); F05D 2220/32 (2013.01)

(58) Field of Classification Search
CPC ....... G02B 23/24; G02B 23/2476; F02C 7/00; F02C 3/04; G01N 21/8803; G01N 21/954; B64F 5/40; F05D 2220/32; F05D 2230/80; F05D 2260/83; F01D 5/005
See application file for complete search history.

(56) References Cited

U.S. PATENT DOCUMENTS

| | | |
|---|---|---|
| 3,503,164 A | 3/1970 | Berry et al. |
| 4,762,118 A | 8/1988 | Lia et al. |
| 5,102,221 A | 4/1992 | Desgranges et al. |
| 5,203,646 A | 4/1993 | Landsberger et al. |
| 5,323,962 A | 6/1994 | Jassby et al. |
| 5,385,102 A | 1/1995 | Villedieu et al. |
| 5,501,156 A | 3/1996 | Richter |
| 5,644,394 A | 7/1997 | Owens |
| 6,156,974 A | 12/2000 | Blasé |
| 6,371,148 B1 | 4/2002 | Tripp |
| 6,481,195 B1 | 11/2002 | Blase |
| 6,698,456 B2 | 3/2004 | Neubauer et al. |
| 6,917,176 B2 | 7/2005 | Schempf et al. |
| 7,171,279 B2 | 1/2007 | Buckingham et al. |
| 7,182,024 B2 | 2/2007 | Pfeiffer |

(Continued)

FOREIGN PATENT DOCUMENTS

| | | |
|---|---|---|
| CN | 101416868 | 4/2009 |
| CN | 102855949 | 1/2013 |

(Continued)

*Primary Examiner* — Thomas Randazzo
(74) *Attorney, Agent, or Firm* — Fitch, Even, Tabin & Flannery LLP

(57) ABSTRACT

A tool system for inserting into a cavity, the tool system including a first continuum having a flexible body defining a connection interface; and a second continuum having a flexible body defining a connection interface; and an engagement mechanism configured to couple the connection interfaces of the first and second continua together to form the tool.

20 Claims, 9 Drawing Sheets

(56) References Cited

U.S. PATENT DOCUMENTS

| | | |
|---|---|---|
| 7,185,407 B2 | 3/2007 | Boyl-Davis et al. |
| 7,258,521 B2 | 8/2007 | Guerra et al. |
| 7,509,735 B2 | 3/2009 | Philip et al. |
| 7,677,181 B2 | 3/2010 | Boyl-Davis et al. |
| 7,718,894 B2 | 5/2010 | Blasé |
| 8,096,030 B2 | 1/2012 | Graichen |
| 8,327,518 B2 | 12/2012 | Korner |
| 8,558,878 B2 | 10/2013 | Bousquet |
| 8,571,711 B2 | 10/2013 | Jacobsen et al. |
| 8,950,439 B2 | 2/2015 | Dudley et al. |
| 9,016,159 B2 | 4/2015 | Kell et al. |
| 9,118,171 B2 | 8/2015 | Blakemore |
| 9,263,866 B2 | 2/2016 | Shimizu |
| 9,329,377 B2 | 5/2016 | Kell et al. |
| 9,399,299 B2 | 7/2016 | Hermey et al. |
| 9,403,244 B2 | 8/2016 | Rautenberg et al. |
| 9,409,292 B2 | 8/2016 | Smith et al. |
| 9,435,750 B2 | 9/2016 | Matsumoto |
| 10,428,993 B2 | 10/2019 | Whitefield et al. |
| 10,525,233 B2 | 1/2020 | Barrish |
| 10,962,345 B2 | 3/2021 | Graham |
| 11,111,813 B2* | 9/2021 | Dede ................. F02C 3/04 |
| 2003/0171650 A1* | 9/2003 | Tartaglia ............ A61B 1/0053 |
| | | 600/114 |
| 2009/0248202 A1 | 10/2009 | Osuka |
| 2012/0067158 A1* | 3/2012 | Kell ..................... B25J 18/06 |
| | | 74/490.04 |
| 2012/0279323 A1* | 11/2012 | Broda ............... G02B 23/2492 |
| | | 73/865.8 |
| 2014/0377010 A1 | 12/2014 | Van Belkom |
| 2015/0059965 A1 | 3/2015 | Geurts |
| 2015/0360629 A1 | 12/2015 | Sekino et al. |
| 2016/0040803 A1 | 2/2016 | Steeger |
| 2016/0221181 A1 | 8/2016 | Goehlich |
| 2017/0023154 A1 | 1/2017 | Jaeker et al. |
| 2017/0239762 A1 | 8/2017 | Roberts et al. |
| 2017/0361470 A1 | 12/2017 | Otero Del Real et al. |
| 2018/0156132 A1 | 6/2018 | Dede et al. |
| 2018/0361960 A1 | 12/2018 | Yamamoto et al. |
| 2019/0190190 A1 | 6/2019 | Bourgeas et al. |
| 2019/0336875 A1 | 11/2019 | Balanchi |
| 2019/0360794 A1 | 11/2019 | Graham et al. |
| 2020/0011181 A1 | 1/2020 | Roberts |
| 2020/0114497 A1 | 4/2020 | Graham |
| 2021/0285374 A1 | 9/2021 | Hawke |
| 2021/0388737 A1 | 12/2021 | Foxall |
| 2022/0071611 A1 | 3/2022 | Xu |

FOREIGN PATENT DOCUMENTS

| | | |
|---|---|---|
| CN | 103811932 | 5/2014 |
| CN | 206600538 | 10/2017 |
| CN | 108601925 | 9/2018 |
| CN | 109498154 | 3/2019 |
| JP | 2008055544 | 3/2008 |
| KR | 20080063707 | 7/2008 |
| WO | 2019210997 | 11/2019 |
| WO | 2019210997 A1 | 11/2019 |

* cited by examiner

INSERTION TOOL

FIELD

The present subject matter relates generally to a tool for inspecting an environment and/or performing maintenance operations on a component within the environment, such as within an annular space in a turbine engine.

BACKGROUND

At least certain gas turbine engines include, in serial flow arrangement, a compressor section including a low pressure compressor and a high-pressure compressor for compressing air flowing through the engine, a combustor for mixing fuel with the compressed air such that the mixture may be ignited, and a turbine section including a high pressure turbine and a low pressure turbine for providing power to the compressor section.

Within one or more of the sections, at least certain gas turbine engines define an annular opening. Certain of these annular openings may vary in size and shape, such that a dedicated, specialized insertion tool must be utilized with each annular opening to extend around and through such annular opening. The aviation service industry continues to demand improvements to insertion tools to increase versatility and reduce the number of individual components required on site during servicing operations.

BRIEF DESCRIPTION

Aspects and advantages of the invention will be set forth in part in the following description, or may be obvious from the description, or may be learned through practice of the invention.

In one exemplary embodiment of the present disclosure, A tool system for inserting into a cavity, the tool system comprising: a first continuum having a flexible body defining a first connection interface; and a second continuum having a flexible body defining a second connection interface; and an engagement mechanism configured to couple the first and second connection interfaces of the first and second continua together to form a tool.

According to another exemplary embodiment, a tool for inserting into a cavity of an aircraft engine, the tool comprising: a flexible first continuum; and a flexible second continuum, wherein the first and second continua are selectively engageable with one another, and wherein when selectively engaged, the first and second continua have a substantially rigid construction.

According to another exemplary embodiment, a method of inserting a tool into a cavity, the method comprising: passing a first continuum through an engagement mechanism; passing a second continuum through the engagement mechanism; and coupling the first and second continua together to form the tool using the engagement mechanism, wherein a shape of the formed tool is defined by a shape of the engagement mechanism.

These and other features, aspects and advantages of the present invention will become better understood with reference to the following description and appended claims. The accompanying drawings, which are incorporated in and constitute a part of this specification, illustrate embodiments of the invention and, together with the description, serve to explain the principles of the invention.

BRIEF DESCRIPTION OF THE DRAWINGS

A full and enabling disclosure of the present invention, including the best mode thereof, directed to one of ordinary skill in the art, is set forth in the specification, which makes reference to the appended figures.

Figure 1:
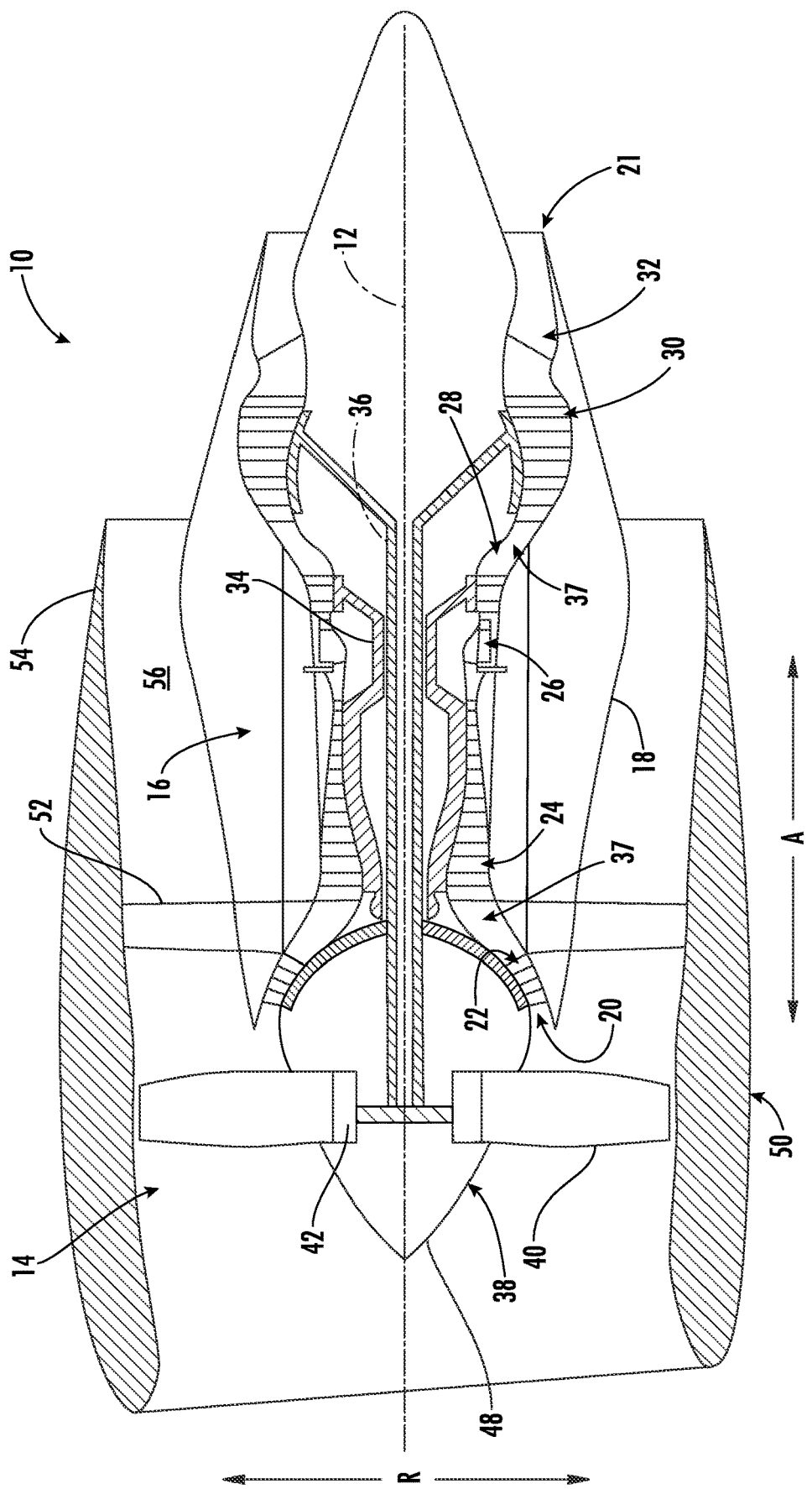
FIG. 1 is a schematic, cross-sectional view of a gas turbine engine in accordance with an exemplary aspect of the present disclosure.

Repeat use of reference characters in the present specification and drawings is intended to represent the same or analogous features or elements of the present invention.

DETAILED DESCRIPTION

Reference now will be made in detail to present embodiments of the invention, one or more examples of which are illustrated in the accompanying drawings. The detailed description uses numerical and letter designations to refer to features in the drawings. Like or similar designations in the drawings and description have been used to refer to like or similar parts of the invention.

The word "exemplary" is used herein to mean "serving as an example, instance, or illustration." Any implementation described herein as "exemplary" is not necessarily to be construed as preferred or advantageous over other implementations. Moreover, each example is provided by way of explanation of the invention, not limitation of the invention. In fact, it will be apparent to those skilled in the art that various modifications and variations can be made in the present invention without departing from the scope of the invention. For instance, features illustrated or described as part of one embodiment can be used with another embodiment to yield a still further embodiment. Thus, it is intended that the present invention covers such modifications and variations as come within the scope of the appended claims and their equivalents.

As used herein, the terms "first," "second," and "third" may be used interchangeably to distinguish one component from another and are not intended to signify location or importance of the individual components. The singular forms "a," "an," and "the" include plural references unless the context clearly dictates otherwise. The terms "coupled," "fixed," "attached to," and the like refer to both direct coupling, fixing, or attaching, as well as indirect coupling, fixing, or attaching through one or more intermediate components or features, unless otherwise specified herein.

The terms "forward" and "aft" refer to relative positions within a gas turbine engine or vehicle, and refer to the normal operational attitude of the gas turbine engine or vehicle. For example, with regard to a gas turbine engine, forward refers to a position closer to an engine inlet and aft refers to a position closer to an engine nozzle or exhaust. The terms "upstream" and "downstream" refer to the relative direction with respect to fluid flow in a fluid pathway. For example, "upstream" refers to the direction from which the fluid flows, and "downstream" refers to the direction to which the fluid flows.

Approximating language, as used herein throughout the specification and claims, is applied to modify any quantitative representation that could permissibly vary without resulting in a change in the basic function to which it is related. Accordingly, a value modified by a term or terms, such as "about," "approximately," and "substantially," are not to be limited to the precise value specified. In at least some instances, the approximating language may correspond to the precision of an instrument for measuring the value, or the precision of the methods or machines for constructing or manufacturing the components and/or systems. For example, the approximating language may refer to being within a 10 percent margin.

Here and throughout the specification and claims, range limitations are combined and interchanged, such ranges are identified and include all the sub-ranges contained therein unless context or language indicates otherwise. For example, all ranges disclosed herein are inclusive of the endpoints, and the endpoints are independently combinable with each other.

In general, an insertion tool in accordance with one or more embodiments described herein can be configured to permit an operator or robotic assembly to inspect a cavity, such as an internal volume of a gas turbine engine. The insertion tool can generally include first and second flexible continua which, when combined, form a substantially rigid structure having selectively arranged geometry in view of the cavity to be inserted into. Each of the flexible continuum may define half of the tool, as seen in the rigid configuration. In certain instances, the insertion tool can be fed into the cavity while simultaneously being shaped by one or more driving or engagement elements described herein. In an embodiment, the geometric shape of the rigid structure can be controlled by the engagement element(s). By way of example, the engagement element(s) can define a desirable shape which can be transferred to the first and second flexible continua to form the rigid structure. Use of various shaped engagement element(s) can allow for selective shaping of the rigid structure in view of the spatial arrangement of the cavity to be inspected or otherwise operated within. In accordance with an embodiment the continua require no dimensional accuracy along the longitudinal direction while simultaneously permitting curvature of the insertion tool. As a result, the insertion tool may be easier and cheaper to manufacture while exhibiting a relatively prolonged operating lifespan.

Referring now to the drawings, wherein identical numerals indicate the same elements throughout the figures, FIG. 1 is a schematic cross-sectional view of a gas turbine engine in accordance with an exemplary embodiment of the present disclosure. More particularly, for the embodiment of FIG. 1, the gas turbine engine is a high-bypass turbofan jet engine 10, referred to herein as "turbofan engine 10." As shown in FIG. 1, the turbofan engine 10 defines an axial direction A (extending parallel to a longitudinal centerline 12 provided for reference) and a radial direction R. The turbofan engine 10 also defines a circumferential direction C (see FIG. 3) extending circumferentially about the axial direction A. In general, the turbofan 10 includes a fan section 14 and a turbomachine 16 disposed downstream from the fan section 14.

The exemplary turbomachine 16 depicted is generally enclosed within a substantially tubular outer casing 18 that defines an annular inlet 20 and an annular exhaust 21. The outer casing 18 encases, in serial flow relationship, a compressor section including a booster or low pressure (LP) compressor 22 and a high pressure (HP) compressor 24; a combustion section 26; a turbine section including a high pressure (HP) turbine 28 and a low pressure (LP) turbine 30; and a jet exhaust nozzle section 32. A high pressure (HP) shaft or spool 34 drivingly connects the HP turbine 28 to the HP compressor 24. A low pressure (LP) shaft or spool 36 drivingly connects the LP turbine 30 to the LP compressor 22. The compressor section, combustion section 26, turbine section, and nozzle section 32 together define a core air flowpath 37 therethrough.

For the embodiment depicted, the fan section 14 includes a fixed pitch fan 38 having a plurality of fan blades 40. The fan blades 40 are each attached to a disk 42, with the fan blades 40 and disk 42 together rotatable about the longitudinal axis 12 by the LP shaft 36. For the embodiment depicted, the turbofan engine 10 is a direct drive turbofan engine, such that the LP shaft 36 drives the fan 38 of the fan section 14 directly, without use of a reduction gearbox. However, in other exemplary embodiments of the present disclosure, the fan 38 may instead be a variable pitch fan, and the turbofan engine 10 may include a reduction gearbox, in which case the LP shaft 36 may drive the fan 38 of the fan section 14 across the gearbox.

Referring still to the exemplary embodiment of FIG. 1, the disk 42 is covered by rotatable front hub 48 aerodynamically contoured to promote an airflow through the plurality of fan blades 40. Additionally, the exemplary turbofan engine 10 includes an annular nacelle assembly 50 that circumferentially surrounds the fan 38 and/or at least a portion of the turbomachine 16. For the embodiment depicted, the nacelle assembly 50 is supported relative to the turbomachine 16 by a plurality of circumferentially-spaced outlet guide vanes 52. Moreover, a downstream section 54 of the nacelle assembly 50 extends over an outer portion of the casing 18 so as to define a bypass airflow passage 56 therebetween. The ratio between a first portion of air through the bypass airflow passage 56 and a second portion of air through the inlet 20 of the turbomachine 16, and through the core air flowpath 37, is commonly known as a bypass ratio.

It will be appreciated that although not depicted in FIG. 1, the turbofan engine 10 may further define a plurality of openings allowing for inspection of various components within the turbomachine 16. For example, the turbofan engine 10 may define a plurality of borescope openings at various axial positions within the compressor section, combustion section 26, and turbine section. Additionally, as will be discussed below, the turbofan engine 10 may include one or more igniter ports within, e.g., the combustion section 26 of the turbomachine 16, that may allow for inspection of the combustion section 26.

It should further be appreciated that the exemplary turbofan engine 10 depicted in FIG. 1 is by way of example only, and that in other exemplary embodiments, the turbofan engine 10 may have any other suitable configuration, including, for example, any other suitable number of shafts or spools, turbines, compressors, etc. Additionally, or alternatively, in other exemplary embodiments, any other suitable turbine engine may be provided. For example, in other exemplary embodiments, the turbine engine may not be a turbofan engine, and instead may be configured as a turboshaft engine, a turboprop engine, turbojet engine, etc.

Figure 2:
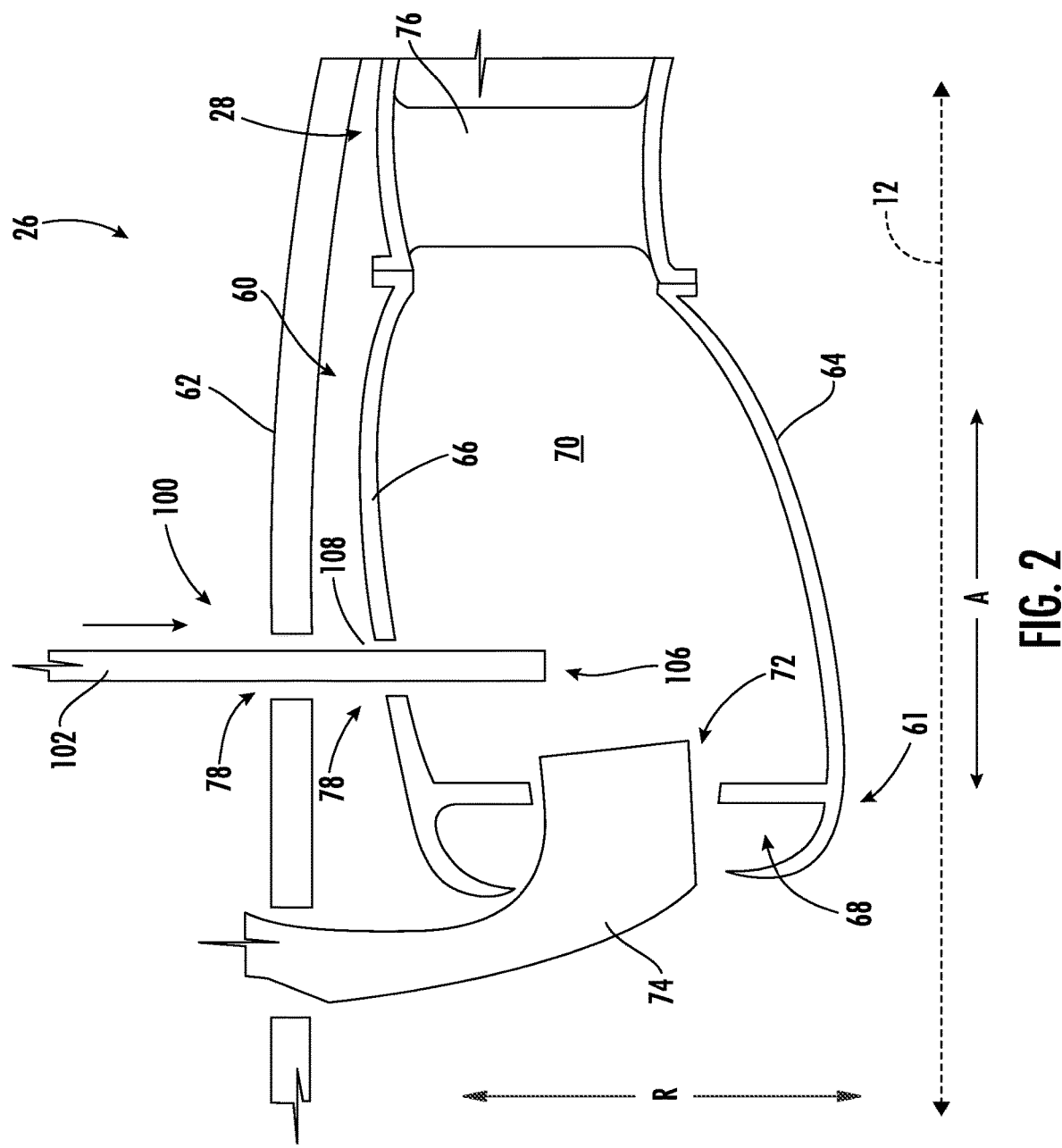
FIG. 2 is a close-up, cross-sectional view of a combustion section of the exemplary gas turbine engine of FIG. 1, including an insertion tool in accordance with an exemplary embodiment of the present disclosure, along an axial direction and a radial direction.

Referring now to FIG. 2, a close-up, schematic view of the combustion section 26 of the turbomachine 16 of the exemplary gas turbine engine 10 of FIG. 1 is provided along with a tool 100 for insertion into an annular section of the engine 10. It will be appreciated that although the tool 100 is depicted in FIG. 2, and described below, as being inserted into a combustion section 26, in other exemplary embodiments, the tool 100 may additionally, or alternatively, be inserted into other areas of the turbofan engine 10 having an annular shape or other shape. For example, the tool 100 may be inserted into annular sections of the compressor section or the turbine section, or alternatively still, other engines or systems altogether. Additionally or alternatively, still, the tool 100 may be inserted into a non-annular section.

As is depicted, the combustion section 26 generally includes a combustor 60 positioned within a combustor casing 62. Additionally, the combustor 60 includes an inner liner 64, an outer liner 66, and a dome 68 together defining at least in part a combustion chamber 70. It will be appreciated that the dome 68, for the embodiment depicted, is an annular dome and the combustor 60 is configured as an annular combustor. In such a manner, the combustion chamber 70 generally defines an annular shape. At a forward end 61, the combustor 60 defines, or rather, the dome 68 defines, a nozzle opening 72, and the combustion section 26 further includes a fuel-air mixer 74, or nozzle, positioned within the nozzle opening 72. The fuel-air mixer 74 is configured to provide a mixture of fuel and compressed air to the combustion chamber 70 during operation of the turbofan engine 10 to generate combustion gases. The combustion gases flow from the combustion chamber 70 to the HP turbine 28, and more specifically, through a plurality of inlet guide vanes 76 of the HP turbine 28.

Notably, although a single nozzle opening 72 and fuel-air mixer 74 is depicted in FIG. 2, the combustor 60 may further include a plurality of circumferentially spaced nozzle openings 72 and a respective plurality of fuel-air mixers 74 positioned within the nozzle openings 72.

In order to initiate a combustion of the fuel and compressed air provided to the combustion chamber 70 by the fuel-air mixer 74, the combustion section 26 typically includes one or more igniters (not installed or depicted) extending through respective igniter openings 78 defined in the combustor casing 62 and the outer liner 66 of the combustor 60. However, when the turbofan engine 10 is not operating, the igniter(s) may be removed and the igniter opening(s) 78 may be utilized for inspecting, e.g., the combustion chamber 70, inlet guide vanes 76 of the HP turbine 28, and/or other components.

More specifically, for the embodiment of FIG. 2, the tool 100 capable of insertion into an annular section of an engine is depicted extending through the pair of igniter openings 78 defined in the combustor casing 62 and the outer liner 66 of the combustor 60.

Figure 3:
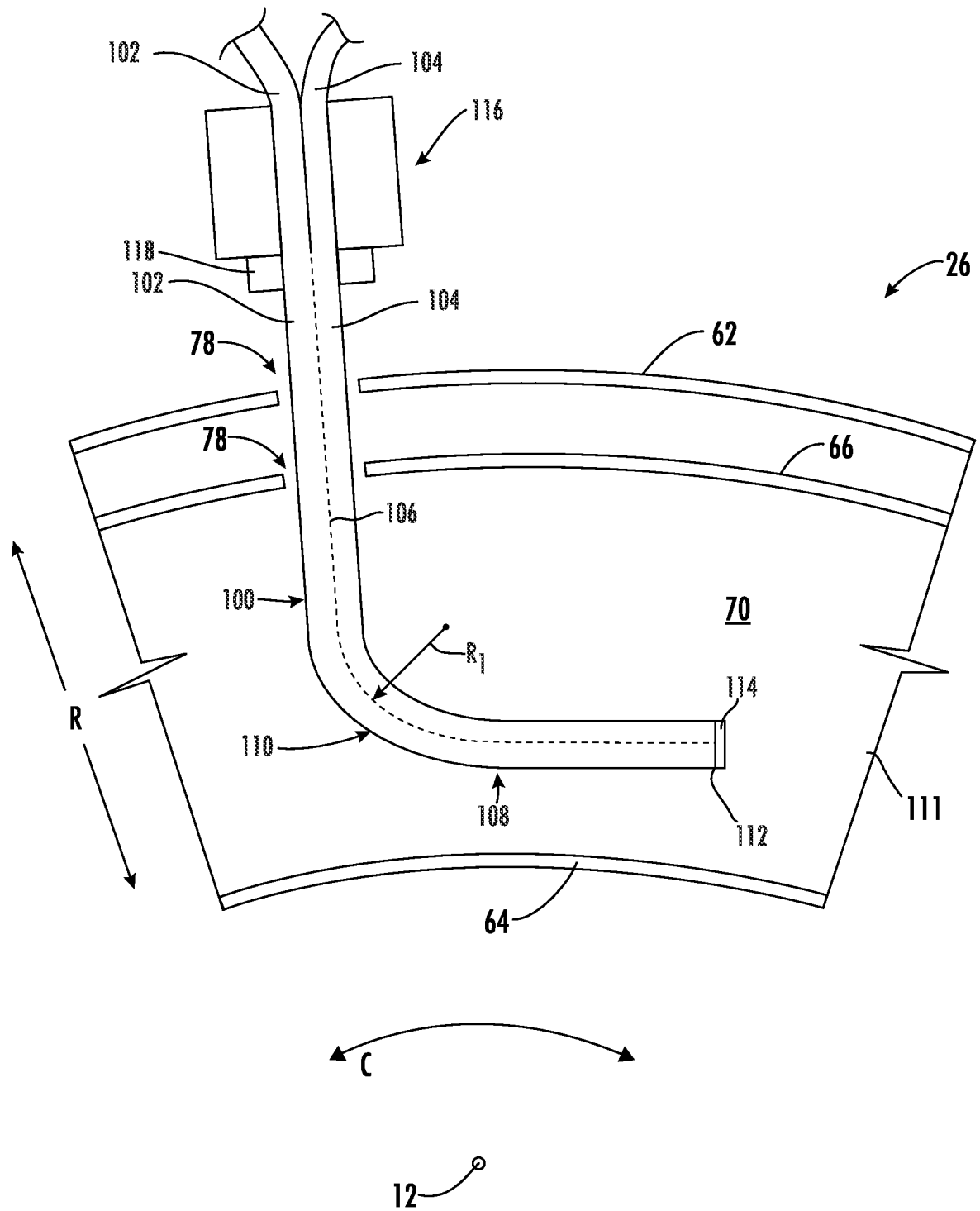
FIG. 3 is another close-up, cross-sectional view of the combustion section of the exemplary gas turbine engine of FIG. 1 including the exemplary insertion tool, along the radial direction and a circumferential direction.

Referring now also to FIG. 3, providing a partial, axial cross-sectional view of the combustion section 26 of FIG. 2, it will be appreciated that the tool 100 generally includes a plurality of continua, such as a first continuum 102 and a second continuum 104, movable into the combustion chamber 70. The first and second continua 102 and 104 can be joined together along a connection interface schematically depicted in FIG. 3 by a dashed line 106. The connection interface 106 can extend continuously along the length of the tool 100. As illustrated in FIG. 3, and according to certain embodiments, the connection interface 106 can remain in a one- or two-dimensional spatial arrangement. That is, the connection interface 106 may not twist, e.g., helically, around a circumference of the tool 100 in a third-dimension of, e.g., a cartesian coordinate system.

In certain instances, the tool 100 can define one or more linear portions 108 and one or more bent portions 110. The bent portions 110 can define radii of curvature, e.g., $R_1$. The radius of curvature of the illustrated bent portion 110 can be disposed within a single plane. That is, for example, as described above, the radius of curvature of the bent portion 110 of the tool 100 can be defined by a single plane.

A distal end 112 of the tool 100 can include an implement, which for the embodiment depicted is a camera 114, to allow for inspection of various components of the combustor 60 and/or high pressure turbine 28. It will be appreciated, however, that the insertion tool 100 may include any other suitable implement, such that the insertion tool 100 may be utilized for any suitable purpose. For example, the insertion tool 100 may be utilized to inspect the interior of the engine using, e.g., the camera 114. Additionally, or alternatively, the insertion tool 100 may include various other tool implements to perform one or more maintenance operations within the interior of the engine (e.g., drilling, welding, heating, cooling, cleaning, spraying, etc.).

Further, the exemplary insertion tool 100 can include a drive assembly 116 for driving the insertion tool 100 into, or out of, the interior of the engine, and more specifically for the embodiment shown, into or out of the combustion chamber 70. The drive assembly 116 may be operably coupled to a controller or other control device, such that a length of the insertion tool 100 within the interior of the engine may be controlled with relative precision by the drive assembly 116.

In an embodiment, the drive assembly 116 can include an engagement mechanism 118 configured to join the first and second continua 102 and 104 together to form the tool 100. In another embodiment, the engagement mechanism 118 and drive assembly 116 can be discrete, i.e., separate, components. For example, the engagement mechanism 118 can be separate from the drive assembly 116 such that the drive assembly 116 interfaces only with the individual first and second continua 102 and 104. The engagement mechanism 118 may be used to selectively join the first and second continua 102 and 104 together to form the tool 100. In certain instances, the engagement mechanism 118 can define one or more selected shapes which can be transferred to the tool 100 during the step of connecting the first and second continua 102 and 104 together. In such a manner, the engagement mechanism 118 can be, e.g., interchanged to permit an operator to adjust the shape of the resulting tool 100. In an embodiment, the engagement mechanism 118 can be selected from a plurality of different engagement mechanisms with at least two of the plurality of different engagement mechanisms having different shapes as compared to one another. The operator can select the appropriately shaped engagement mechanism from the plurality of different engagement mechanisms based on the engine being serviced.

In an embodiment, the engagement mechanism 118 can be a variable shaped engagement mechanism. In such a manner, the operator can selectively shape the engagement mechanism 118 to achieve a desired shape of the resulting tool 100. By way of example, the variable shaped engagement mechanism can include an actuated flexible or hinged section which permits the operator to select desired bend shapes and sizes for the environment being operated within.

Figure 4:
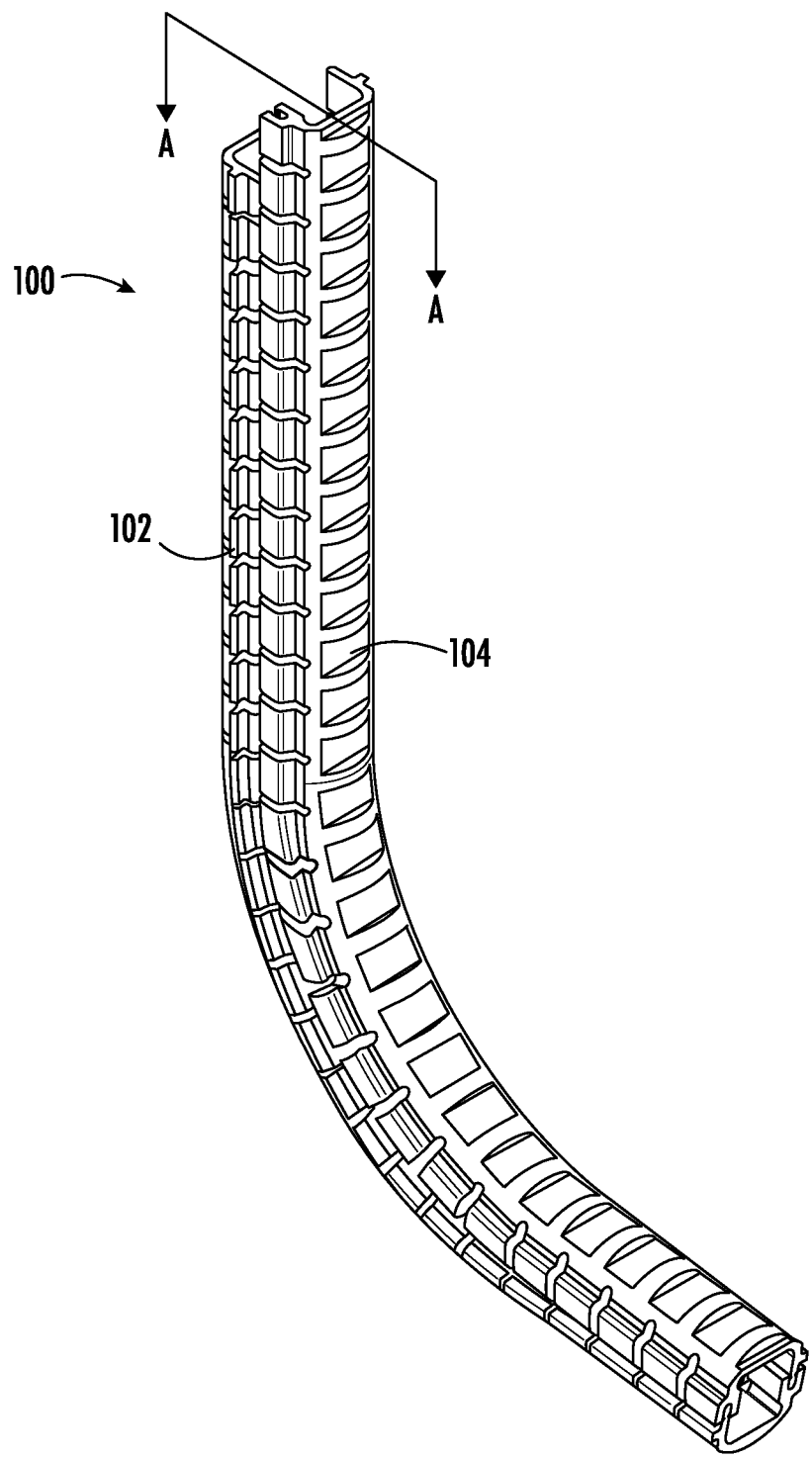
FIG. 4 is a perspective view of an insertion tool in accordance with an exemplary embodiment of the present disclosure.

FIG. 4 illustrates a perspective view of the tool 100 as seen in accordance with an exemplary embodiment during a process of joining the first and second continua 102 and 104 together so as to form a substantially rigid structure for performing a service, e.g., inspection and/or operation, in a cavity of equipment, such as aircraft engines. In this regard, a shape of the upper portion of the tool 100 is not yet defined, while the lower portion of the tool 100 includes interconnected first and second continua 102 and 104, thus defining the shape of the lower portion of the tool 100.

Figure 5:
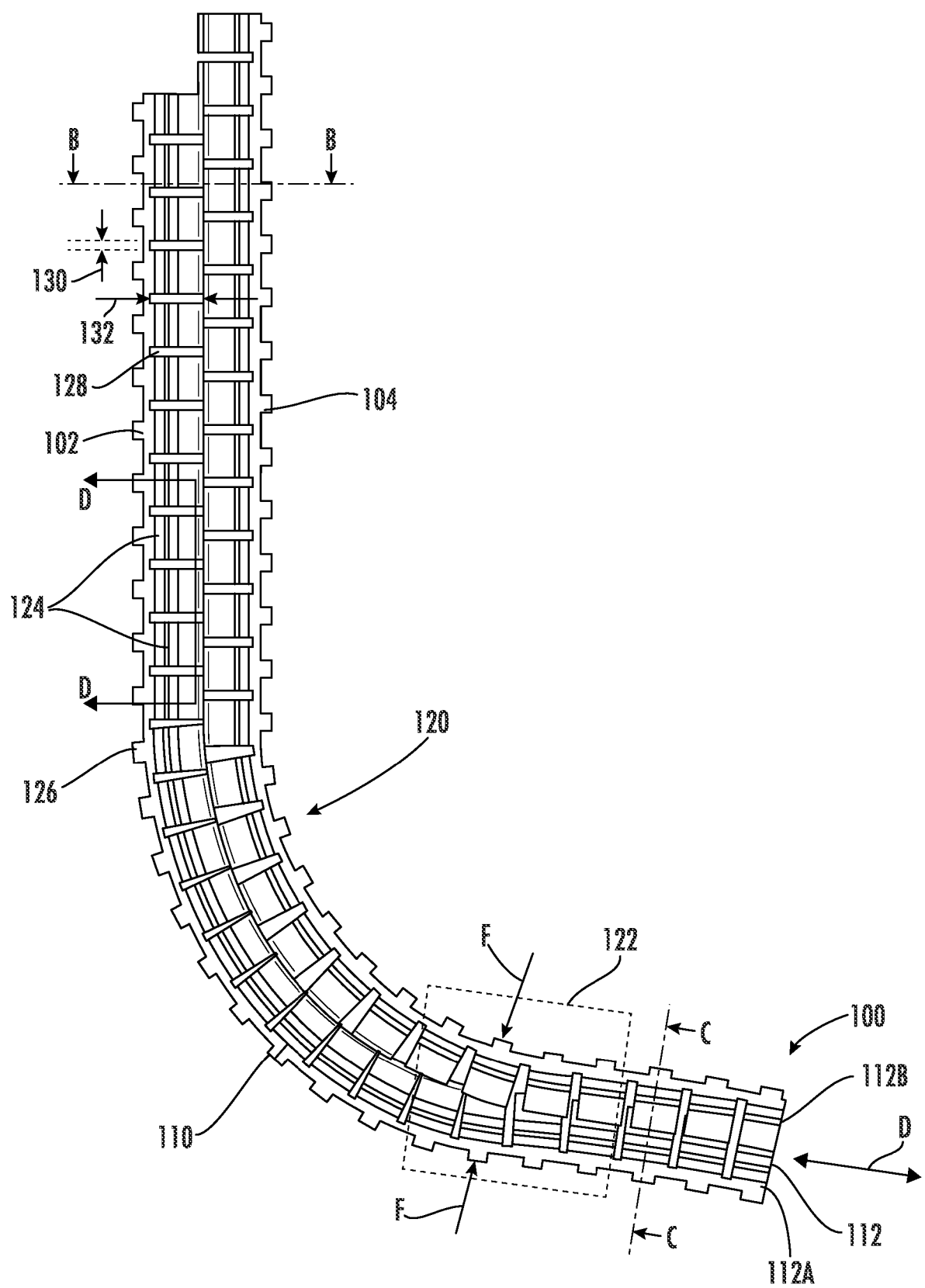
FIG. 5 is a cross-sectional side view of a first continuum and a second continuum of an insertion tool, as seen along Line A-A in FIG. 4, in accordance with an exemplary embodiment of the present disclosure.

FIG. 5. illustrates a cross-sectional side view of the first continuum 102 and the second continuum 104 of the insertion tool 100 in accordance with an exemplary embodiment of the present disclosure as seen along Line A-A in FIG. 4. The tool 100 is generally travelling in a direction D into or away from an area of interest, e.g., an inspection area of an engine. As illustrated, the first and second continua 102 and 104 are separate at a first location 120 and join together to form the tool 100 at a mesh point 122, e.g., where the aforementioned engagement mechanism 118 (FIG. 3) is located. In certain instances, the mesh point 122 can include an area where one or more coupling force(s), e.g., inward forces F, transverse to longitudinal lengths of the first and second continua 102 and 104, are applied to the first and second continua 102 and 104. In an embodiment, the coupling force can be generated, for example, at a discrete location within the mesh point 122. In another embodiment, the coupling force can be generated at a plurality of locations within the mesh point 122 or along a continuous length of the mesh point 122. That is, for example, the forces F can be generated by a ramped interface that progressively narrows the distance between the first and second continua 102 and 104. The mesh point 122 can transition the first and second continua 102 and 104 from a detached (i.e., decoupled) configuration to an attached configuration so as to form the tool 100.

As illustrated in FIG. 5, the distal end 112 of the tool 100 can be formed, at least in part, by both the first and second continua 102 and 104. For example, the first and second continua 102 and 104 can be aligned such that half of the distal end 112 is defined by the first continuum 102 and the other half of the distal end 112 is defined by the second continuum 104. In such a manner, individual distal ends 112A and 112B of the first and second continua 102 and 104, respectively, can be coplanar. As a result, inclusion of one or more bent portions, such as, e.g., bent portion 110, can cause the relative lengths of the first and second continua 102 and 104 actively forming part of the rigid portion of the tool 100 to be different from one another. As used herein, active parts of the tool 100 may refer to those portions of the tool 100 where the first and second continua 102 and 104 are coupled together to form the substantially rigid tool. Conversely, inactive parts of the tool 100 can refer to those portions of the first and second continua 102 and 104 that are not joined together. As illustrated in FIG. 5, the second continuum 104 has a shorter distance to travel around the bent portion 110 as a result of being on a side of the tool 100 radially inside of the first continuum 102. Accordingly, more of the first continuum 102 is required to maintain the tool 100 with the bent portion 110. Conversely, introduction of a second bent portion (not illustrated) in the tool 100 having an equal but opposite radius of curvature to the bent portion 110 (e.g., an S-curve formed of equal bend radii) may result in the effective lengths of the first and second continua 102 and 104 being equal as measured upstream of the second bent portion.

After passing through the mesh point 122, the tool 100 can have a rigid construction. That is, the profile of the tool 100 (e.g., any curvatures defined therein) can remain relatively fixed downstream of the mesh point 122. In such a manner, the curvature of the tool 100 may be determined in anticipation of the shape and/or size of the cavity being inspected or operated on by the tool 100.

To facilitate bending of the tool 100, at least one of the first and second continua 102 and 104, such as both the first and second continua 102 and 104, can include a plurality of C-shaped portions 124 coupled together through an elongated structure 126. The elongated structure 126 may extend continuously along the length of the first and/or second continua 102 and 104. In certain instances, the elongated structure 126 may include a single elongated structure extending along the entire length of the first and/or second continua 102 and 104. In other instances, the elongated structure 126 can include a plurality of elongated structures joined together.

In an embodiment, at least one of the first and second continua 102 and 104, such as both the first and second continua 102 and 104, can include a single, e.g., monolithic, component. For example, the first continuum 102 can include a single-piece structure comprising a single elongated structure 126 and a plurality of interspaced C-shaped portions 124. In other embodiments, at least one of the first and second continua 102 and 104 can include a multi-piece construction. For instance, the elongate structure 126 can include a first material and the C-shaped portions 124 can include a second material different than the first material. By way of example, the elongated structure 126 can include a more readily deformable material as compared to the material of the C-shaped portions 124. The C-shaped portions 124 can include more resilient materials as compared to the elongated structure 126. One exemplary material for the elongated structure 126 includes spring steel. Other materials include stainless steel, nitinol, beryllium copper, and other materials which exhibit generally elastic behavior. In certain instances, at least one of the C-shaped portions 124 can be attached to the elongated structure 126 through over-molding, fusion, adhesive, and the like.

While flexure of the first continuum 102 may occur at any location along the length thereof, in certain instances a majority of bending can occur at the elongated structure 126 between adjacent C-shaped portions 124. The relative amount of obtainable flexure of the tool 100 can be determined at least in part by dimensions of gaps 128 between adjacent C-shaped portions 124. For instance, the relative lengths 130 and widths 132 of the gaps 128 can define a maximum bend angle between adjacent C-shaped portions 124. Narrow gaps 128 in the direction 130 may cause reduced bending. Similarly, long gaps 128 in the direction 132 may reduce bending. While the gaps 128 are shown in FIG. 5 as having equal dimensions and geometry as compared to one another, in certain instances, the gaps 128 may define variable sizing and/or variable geometry as compared to one another.

Figure 6:
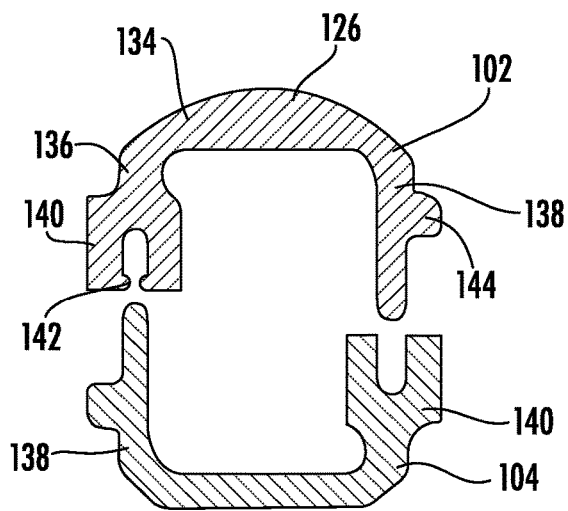
FIG. 6 is a cross-sectional view of the first and second continua of the insertion tool of FIG. 5, as seen along Line B-B, in accordance with an exemplary embodiment of the present disclosure.
Figure 7:
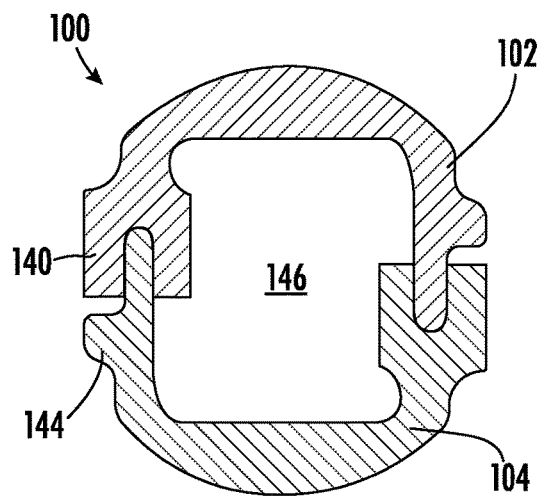
FIG. 7 is a cross-sectional view of the first and second continua of the insertion tool of FIG. 5, as seen along Line C-C, in accordance with an exemplary embodiment of the present disclosure.

FIG. 6 illustrates a cross-sectional view of the first and second continua 102 and 104 of the insertion tool 100 of FIG. 5, as seen along Line B-B, in accordance with an exemplary embodiment of the present disclosure. The portion of the first and second continua 102 and 104 illustrated in FIG. 6 is upstream of the mesh point 122. Accordingly, the first and second continua 102 and 104 are not yet joined together. FIG. 7 illustrates a cross-sectional view of the first and second continua 102 and 104 of the insertion tool 100 of FIG. 5, as seen along Line C-C, in accordance with an exemplary embodiment of the present disclosure. The portion of the first and second continua 102 and 104 illustrated in FIG. 7 is downstream of the mesh point 122. Accordingly, the first and second continua 102 and 104 are joined together to form the tool 100.

As illustrated in the exemplary embodiment of FIGS. 6 and 7, the first and second continua 102 and 104 may be generally the same as compared to one another. For instance, the first and second continua 102 and 104 may be reflectively or rotationally symmetrical with one another. Reference made hereinafter to the first continuum 102, or features thereof, may thus be applicable to both the first and second continuum 102 and 104. Alternatively, one or more features of the first and second continua 102 and 104 may be different from one another.

Referring to FIG. 6, the first continuum 102 can include a generally C-shaped body 134. The elongated structure 126 can form, or be part of, the middle section of the C-shaped body 134. First and second arms 136 and 138 can extend from the middle section of the C-shaped body 134, e.g., from the elongated structure 126. In certain embodiments, the lengths of the first and second arms 136 and 138 can be generally the same as one another. In other embodiments, the lengths of the first and second arms 136 and 138 can be different as compared to one another.

In the illustrated embodiment, the first arm 136 includes a receiver 140 disposed at an end thereof and configured to receive a portion of the second continuum 104. The receiver 140 is illustrated as a channel having a U-shape into which a second arm 138 of the second continuum 104 can be inserted. The receiver 140 can include one or more features 142 configured to increase the necessary force required to decouple the first and second continua 102 and 104 from one another. In the illustrated embodiment, the one or more features 142 includes a projection extending into the U-shaped channel so as to form an interference fit with the second arm 138 of the second continuum 104. In other embodiments, the one or more features 142 can include any one or more of tines, barbs, scallops, undulations, castellations, or other geometry configured to grip the second arm 138 of the second continuum 104. The one or more features 142 may operate in multiple directions to prevent undesirable movement between the first and second continua 102 and 104. For instance, in addition to maintaining the first and second continua 102 and 104 in engagement with one another, the one or more features 142 can prevent longitudinal displacement between the first and second continua 102 and 104.

In the illustrated embodiment, the second arm 138 has a generally linear geometry configured to extend into a receiver 140 of the second continuum 104. A guide feature 144 may be disposed on the second arm 138 to prevent overinsertion of the second arm 138 into the receiver 140. Moreover, the guide feature 144 may be useful for an observer or control system in preventing underinsertion. That is, the observer or control system can determine if the guide feature 144 is too far spaced apart from the receiver 140 in the installed state. Gaps between the guide feature 144 and receiver 140 exceeding a threshold distance may be indicative of non-fully engaged first and second continua 102 and 104.

In other embodiments, the contact interface 106 may be formed by one or more additional or other methods different than the aforementioned frictional or interference fits. For example, the contact interface 106 may be formed through electrostatic adhesion, magnetic attraction, chemical adhesion (e.g., thermal set glue), through van der Waals forces (e.g., gecko-type, sticky feet), and the like. Moreover, these contact interfaces 106 may be formed using a plurality of different types of attachment protocol.

Referring to FIG. 7, the guide feature 144 may remain spaced apart from the receiver 140 in the engaged, i.e., coupled, configuration. The guide feature 144 may form an interface for one or more components to operate on the tool 100. For instance, the gap between the guide feature 144 and receiver 140 may permit a tool to slide between the guide feature 144 and receiver 140 to separate the first and second continua 102 and 104 from one another.

In the coupled configuration illustrated in FIG. 7, the first and second continua 102 and 104 can combine to form a rigid structure of the tool 100. A volume 146 can be defined within the first and second continua 102 and 104. The volume 146 can permit routing of one or more tooling components or tooling support cables, wires, and the like. The size of the volume 146 may remain substantially constant along the length of the tool 100.

Figure 8:
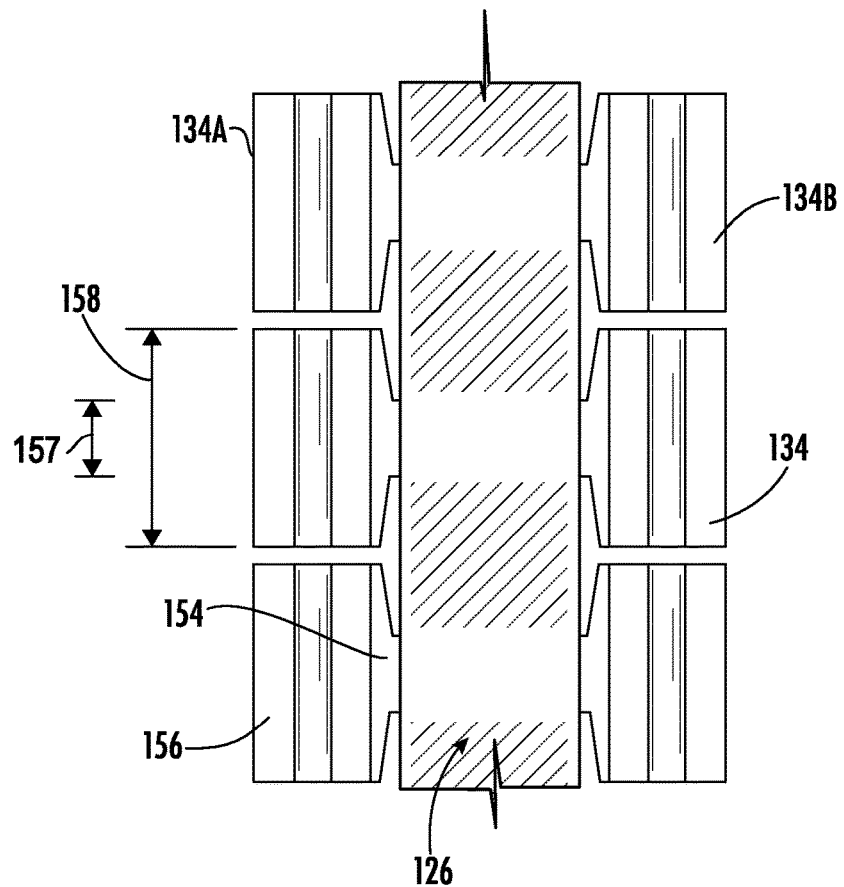
FIG. 8 is an elevation view of the first continuum of the insertion tool of FIG. 5, as seen along Line D-D, in accordance with an exemplary embodiment of the present disclosure.

FIG. 8 illustrates an elevation view of the first continuum 102 as seen along Line D-D in FIG. 5. The elongated structure 126 is shown having a plurality of C-shaped portions 134 extending therefrom. In the exemplary embodiment depicted in FIG. 8, each C-shaped portion 134 includes a first portion 134A and a second portion 134B spaced apart by the elongated structure 126. In certain instances, the first and second portions 12dA 134A and 134B can be reflectively symmetrical in arrangement about the elongated structure 126. In other instances, the first and second portions 134A and 134B can be staggered or longitudinally offset from one another along a longitudinal direction of the first continuum 102. It is noted that complete longitudinal offset between the first and second portions 134A and 134B may reduce flexibility of the elongated structure 126 of the first and second continua 102 and 104. Additional features, such as cutouts and the like, may be utilized to re-introduce flexibility into the elongated structure 126.

At least one of the first and second portions 134A and 134B of at least one of the C-shaped portions 134 can have a narrow base 154 and a wider head 156. The narrow base 154 may facilitate easier bending of the first continuum 102 by reducing a length of the elongated structure 126 fixed to the C-shaped portions 134. By way of example, the narrow base 154 can define a longitudinal dimension 157 that is no greater than 99% the longitudinal dimension 158 of the wider head 156, such as no greater than 98% the longitudinal dimension 158, such as no greater than 97% the longitudinal dimension 158, such as no greater than 96% the longitudinal dimension 158, such as no greater than 95% the longitudinal dimension 158, such as no greater than 90% the longitudinal dimension 158, such as no greater than 80% the longitudinal dimension 158, such as no greater than 70% the longitudinal dimension 158, such as no greater than 60% the longitudinal dimension 158, such as no greater than 50% the longitudinal dimension 158. In certain instances, the base 154 can taper from a narrowest point closest to the elongated structure 126 to a widest part adjacent to the head 156.

Figure 9:
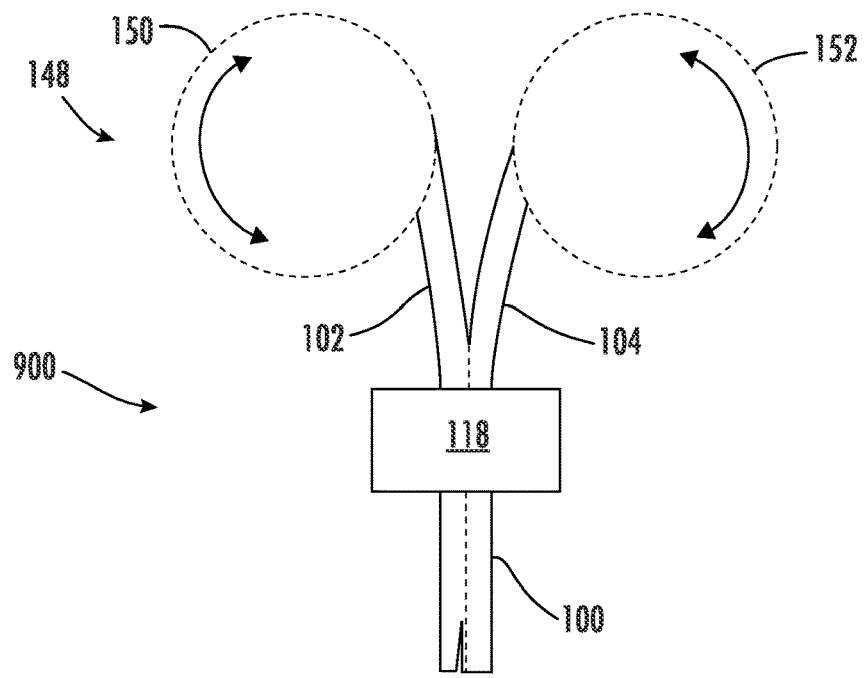
FIG. 9 is a schematic view of a system including an exemplary insertion tool in accordance with an exemplary embodiment of the present disclosure.

FIG. 9 illustrates a tool system 900 for forming the tool 100 in accordance with one or more exemplary embodiments described herein. The tool system 900 includes the aforementioned engagement mechanism 118 for joining the first and second continua 102 and 104 together. As depicted in FIG. 9, the tool system 900 comprises a storage area 148 configured to store portions of at least one of the first and second continua 102 and 104 that are not actively part of the tool 100. Portions of the first and second continua 102 and 104 that are not actively part of the tool include those portions of the continua 102 and 104 that are not yet joined together. For example, a first portion of the first continuum 102 can be disposed on a first side of the engagement mechanism 118 (the first side being associated with the tool 100) and a second portion of the first continuum 102 can be disposed on a second side of the engagement mechanism 118. The second portion can correspond with the portion of the continuum 102 not actively part of the tool 100 at a given moment. Lengths of the first and second portions can change inversely with respect to one another.

In an embodiment, the storage area 148 can include a first storage area 150 for storing inactive portions of the first continuum 102 and a second storage area 152 for storing inactive portions of the second continuum 104. In certain instances, the first and second storage areas 150 and 152 can be configured to store the first and second continua 102 and 104, respectively, in rolled configurations. That is, the deflectable radius of curvature of the first and second continua 102 and 104 can permit rolled, space-efficient storage for those portions of the first and second continua 102 and 104 not being actively used by the tool 100. By way of example, at least one of the first and second storage areas 150 and 152 can include a rotatable element, such as a rotatable spool. As the tool 100 is biased away from the engagement mechanism 118, the first and second storage areas 150 and 152 can unwind the first and second continua 102 and 104, respectively, to feed the engagement mechanism 118 and elongate the tool 100. Similarly, as the tool 100 is biased toward the engagement mechanism 118, the first and second storage areas 150 and 152 can wind the first and second continua 102 and 104, respectively to store the first and second continua 102 and 104.

In another embodiment, at least one of the first and second storage areas 150 and 152 can operate through a different mechanism as compared to the aforementioned rotational operational protocol. For example, the first and second continua 102 and 104 can be laid linearly in a storage area, optionally including bent portions to create a zigzag, or other similar, pattern.

In certain instances, at least one of the first and second storage areas 150 and 152 can be driven. That is, unwinding and/or winding the first and second continua 102 and 104 can be at least in part performed by rotatably biasing the first and/or second storage areas 150 and 152. In other instances, at least one of the first and second storage areas 150 and 152 can be passive. In such a manner, winding and/or unwinding the first and second continua 102 and 104 relative to the first and second storage areas 150 and 152, respectively, can be performed by a separate component, such as the driving mechanism 116.

In an embodiment, at least one of the first and second continua 102 and 104 may remain at least partially engaged with the engagement mechanism 118 when in a fully stored position, i.e., when the first and second continua 102 and 104 are not actively used to form the tool 100. That is, the first and/or second continua 102 and 104 may not be fully stored (e.g., wound) on the first and second storage areas 150 and 152 in the stored position. Instead, the distal ends 112A and 112B can remain coupled with the engagement mechanism 118. This may facilitate easier formation of a future tool 100 without requiring refeeding of the first and second continua 102 and 104 thereinto.

After finishing each successive use of the tool 100, the first and second continua 102 and 104 may be retracted at least partially into the first and second storage areas 150 and 152. The distal ends 112A and 112B may be maintained at relatively fixed longitudinal locations with respect to one another in the stored position.

In an embodiment, at least one of the first and second continua 102 and 104 can define a length no less than the length of the tool 100. In a particular embodiment, both the first and second continua 102 and 104 can define lengths greater than the length of the tool 100.

Figure 10:
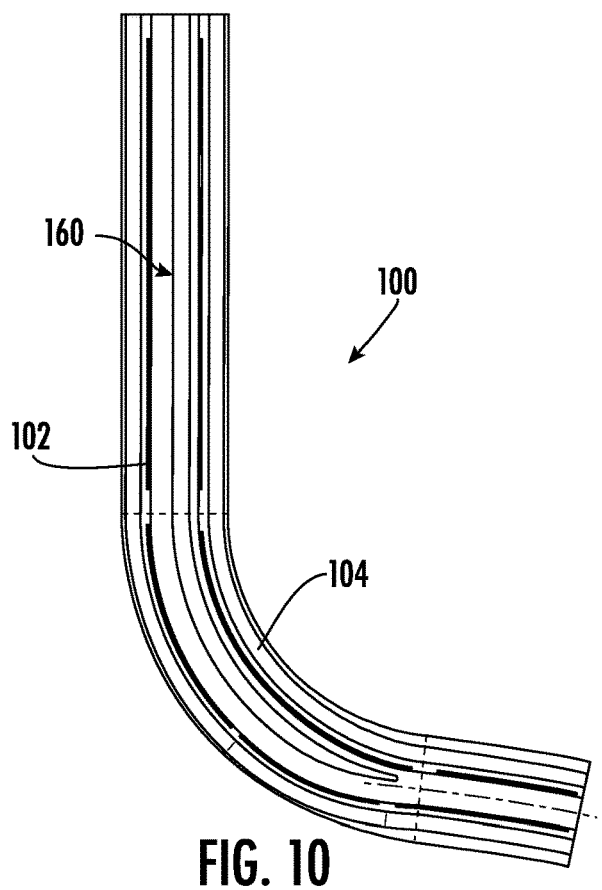
FIG. 10 is a cross-sectional view of an insertion tool in accordance with an exemplary embodiment of the present disclosure.

FIG. 10 illustrates a cross-sectional view of an embodiment of the insertion tool 100 including a detachment element 160 disposed in alignment with the first and second continua 102 and 104 so as to separate the first and second continua 102 and 104 from one another as they are removed from the cavity. By way of non-limiting example, the detachment element 160 can include a wedge configured to be disposed between the first and second continua 102 and 104. As the tool 100 is biased in a direction toward the detachment element 160, the wedged configuration of the detachment element 160 (or another suitable detachment protocol) can cause the first and second continua 102 and 104 to separate from one another.

Figure 11:
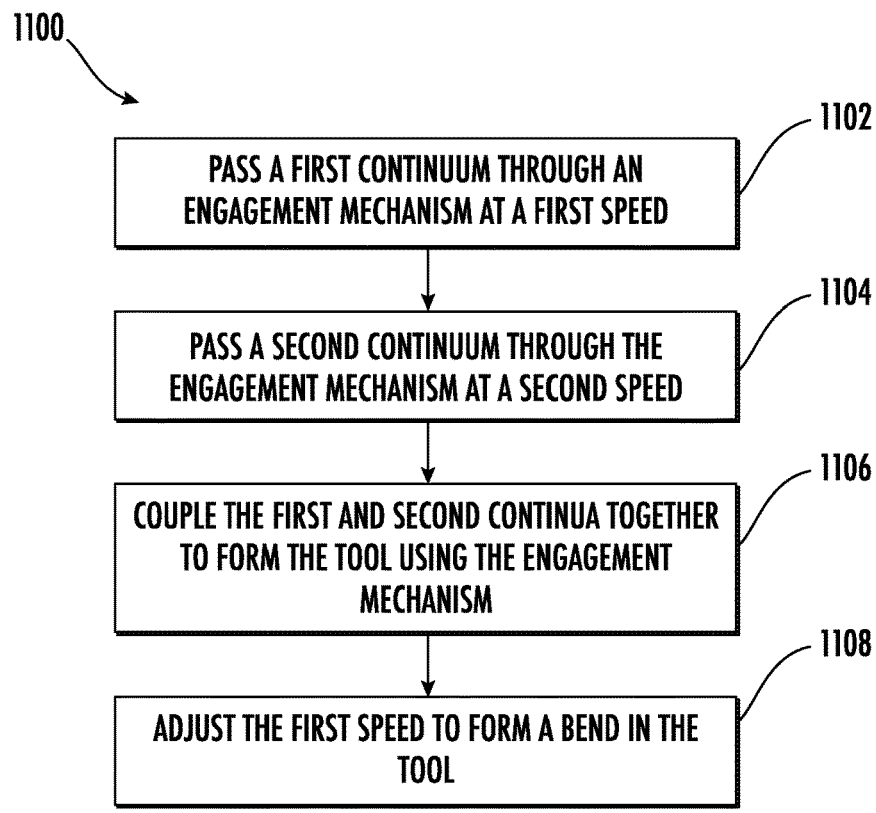
FIG. 11 is a flowchart of a method of inserting a tool into a cavity in accordance with an exemplary embodiment of the present disclosure.

FIG. 11 is a flow chart of a method 1100 of inserting a tool into a cavity. The method 1100 includes a step 1102 of passing a first continuum through an engagement mechanism at a first speed and a step 1104 of passing a second continuum through the engagement mechanism at a second speed. The relative difference between the first and second speeds at steps 1102 and 1104 can determine a relative curvature of the tool. For example, when the first speed is greater than the second speed, the first continuum may form an outer surface of the curvature of the tool, i.e., the radius of curvature of the first continuum is greater than a radius of curvature of the second continuum. Conversely, when the second speed is greater than the first speed, the second continuum may form an outer surface of the curvature of the tool, i.e., the radius of curvature of the second continuum is greater than the radius of curvature of the first continuum. Where the first and second continua are stored in a rolled configuration, the steps 1102 and 1104 may be performed by unwinding the first and second continua from the rolled configuration. This may include biasing the spool on which at least one of the first and second continua are stored, or pulling the first and/or second continua from the spool by another driving mechanism.

The method 1100 further includes a step 1106 of coupling the first and second continua together to form the tool using the engagement mechanism. Coupling the first and second continua together when the first and second continua are travelling at different speeds results in the curvature being selectively maintained within the tool. The step 1106 of coupling the first and second continua together using the engagement mechanism may be performed at a location near the cavity, e.g., adjacent to the cavity. As the tool is being formed at step 1106, a distal end thereof can pass into the cavity while the first and second continua pass through the engagement mechanism. That is, a leading portion of the tool can enter the cavity as a trailing portion behind the leading portion is being formed by the engagement mechanism.

The method 1000 further includes a step 1108 of adjusting the first speed to form a bend in the tool. The bend formed at step 1108 can have a lesser or greater radius of curvature as compared to the radius of curvature of the tool at an immediately adjacent location. The step 1108 of adjusting the first speed can be performed, for example, to achieve a certain geometry necessary to insert the tool into the cavity so as to clear obstacles and structures therein.

Figure 12:
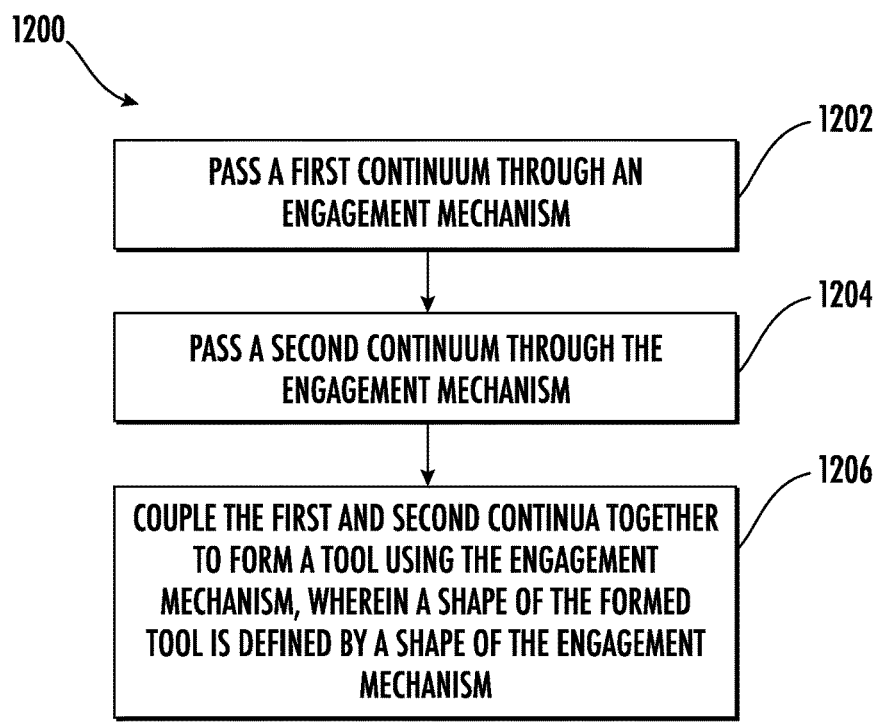
FIG. 12 is a flowchart of a method of inserting a tool into a cavity in accordance with an exemplary embodiment of the present disclosure.

FIG. 12 is a flow chart of a method 1200 of inserting a tool into a cavity in accordance with another exemplary embodiment. The method 1200 includes a step 1202 of passing a first continuum through an engagement mechanism and a step 1104 of passing a second continuum through the engagement mechanism. The method further includes a step 1206 of coupling the first and second continua together to form a tool using the engagement mechanism. The shape of the formed tool is defined by a shape of the engagement mechanism. In one or more instances, the operator can selectively change the engagement mechanism to change the shape imparted onto the formed tool at step 1206. More particularly, the operator can select the engagement mechanism from a plurality of engagement mechanisms, where at least two of the plurality of engagement mechanisms have different shapes as compared to one another. The selective change between two or more of the plurality of engagement mechanisms can occur, for example, when the operator is moving the tool between different cavities being inspected or even during the inspection of a single cavity. For example, the operator may change to a different engagement mechanism when inspecting a different engine or within the inspection process of a single engine.

Figure 13:
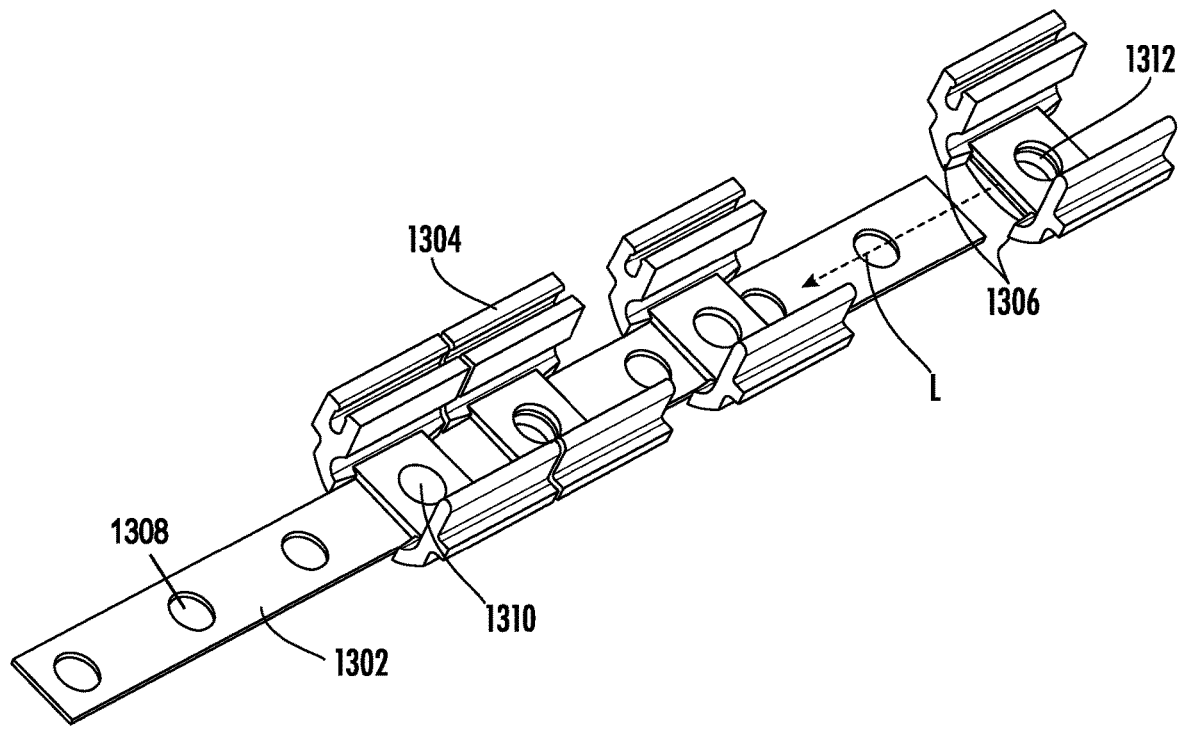
FIG. 13 is a perspective view of a continuum of an insertion tool in accordance with another exemplary embodiment of the present disclosure.
Figure 14:
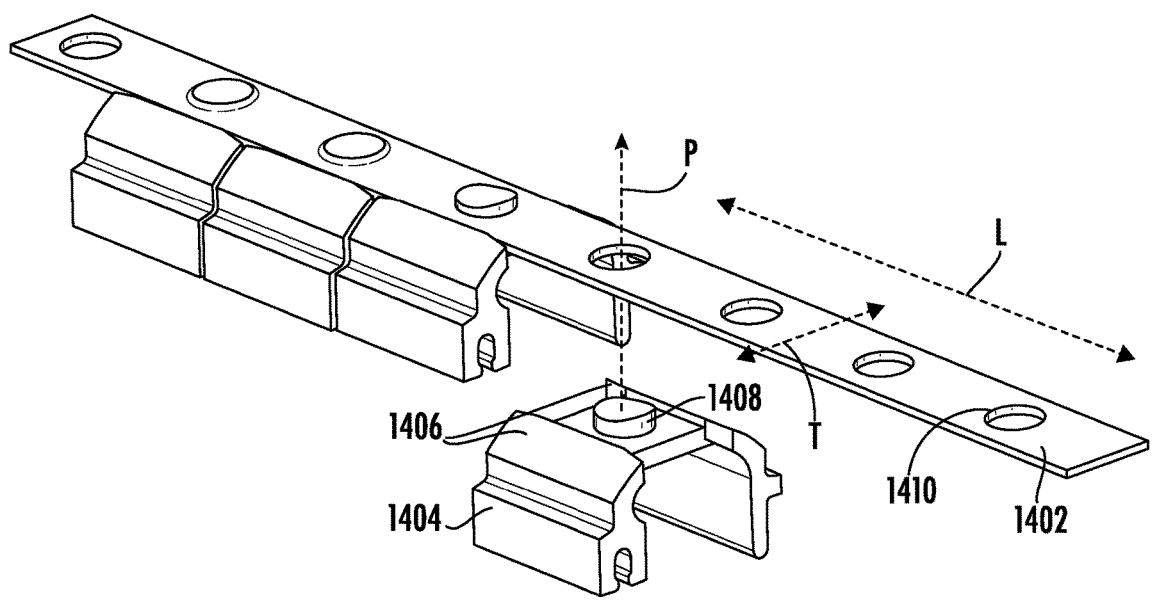
FIG. 14 is a perspective view of a continuum of an insertion tool in accordance with another exemplary embodiment of the present disclosure.

Referring now to FIGS. 13 and 14, in accordance with one or more embodiments, the aforementioned insertion tool 100 can be formed at least in part from one or more continua that have a multi-piece construction. Referring initially to FIG. 13, an exemplary continuum 1300 is depicted including an elongated structure 1302 configured to receive bodies 1304, e.g., C-shaped bodies. The elongated structure 1302 and bodies 1304 can include discrete, i.e., separate, elements which can be joined together to form the continuum 1300. The bodies 1304 can be similar in engagement protocol to the generally C-shaped body 134 previously described. In such a manner, the bodies 1304 can be joined together to form the insertion tool 100 in a manner as previously described.

In certain instances, the bodies 1304 can translate, e.g., slide, relative to the elongated structure 1302 in a longitudinal direction L. In such a manner, the bodies 1304 can be translated relative to the elongated structure 1302 during formation of the continuum 1300. By way of non-limiting example, the bodies 1304 can include guide features 1306 which slide along the elongated structure 1302. The guide features 1306 can include one or more rails, slots, and the like which are arranged to guide the bodies 1304 relative to the elongated structure 1302. In an embodiment, at least one of the bodies 1304 can be installed at a longitudinal end of the elongated structure 1302. In another embodiment, at least one of the bodies 1304 can be installed on the elongated structure 1302 at a location spaced apart from the longitudinal ends thereof.

The elongated structure 1302 can include a plurality of receiving areas 1308, with at least some of the receiving areas 1308, e.g., all of the receiving areas 1308, being configured to receive one or more bodies 1304. The bodies 1304 can be translated relative to the elongated structure 1302 until aligning with an appropriate receiving area 1308. The receiving areas 1308 can generally include mechanisms for engagement with the bodies 1304. By way of non-limiting example, at least one of the receiving areas 1308 can include an opening extending into, such as through, the elongated structure 1302. In the illustrated embodiment, at least some of the bodies 1304 can define an interface configured to be secured to the elongated structure 1302 through the use of a connection component 1310. The interface can include, for example, an opening 1312 configured to be aligned with one or more of the receiving areas 1308. In certain instances, the receiving areas 1308 can be equally spaced apart from one another. The spacing between adjacent receiving areas 1308 and 1308 can be dimensioned such that the bodies 1304 are operationally disposed to permit flexure of the continuum 1300 during formation of the rigid portion of the tool 100.

The connection component 1310 can secure the opening 1312 of the body 1304 with the receiving area 1308 of the elongated structure 1302. In a particular embodiment, the connection component 1310 can be engaged at the interface by sliding the connection component 1310 through at least a portion of the body 1304 and the elongated structure 1302. By way of example, the connection component 1310 can secure the interface by translating in a direction generally perpendicular to the longitudinal direction L which the bodies 1304 translate relative to the elongated structure 1302. In an embodiment, the interface between the connection component 1310 and at least one of the elongated structure 1302 and body 1304 can include a locking interface configured to prevent accidental removal of the connection component 1310, a tactile indicator of proper seating of the connection component 1310, or both. With the bodies 1304 secured in place relative to the elongated structure 1302, the continuum 1300 can be joined with another continuum to form the tool 100.

FIG. 14 illustrates a continuum 1400 having a different multi-piece construction in accordance with another exemplary embodiment. Unlike the embodiment illustrated in FIG. 13 where the bodies 1304 translate in the longitudinal direction L relative to the elongated structure 1302, the continuum 1400 depicted in FIG. 14 permits installation of one or more bodies 1404 along an elongated structure 1402 in a direction generally perpendicular to the longitudinal direction L. As illustrated, the bodies 1404 can be installed on the elongated structure 1402 by translating the bodies 1404 in a direction P perpendicular, or generally perpendicular, with the longitudinal direction L of the elongated structure 1402. Guide features 1406 can align the bodies 1404 relative to the elongated structure 1402. For example, the guide features 1406 can align, e.g., center, each body 1404 relative to a transverse axis T, such that an engagement feature 1408 of the body 1404 is aligned with a receiving area 1410 of the elongated structure 1402. The engagement feature 1408 can engage with the receiving area 1410 to secure the body 1404 to the elongated structure 1402.

In an embodiment, the engagement feature 1408 can be fixed to the receiving area 1410 through a mechanical and/or chemical fastener. For example, the engagement feature 1408 can be crimped, fastened, pinned, welded, heat fused, or otherwise mechanically attached to the receiving area 1410 and/or chemically fastened thereto, e.g., by adhesive bonding.

It should be understood that the embodiments illustrated in FIGS. 13 and 14 are not exclusive and that certain aspects of each embodiment can be utilized together in a non-illustrated embodiment. Multi-piece constructed continuums may permit use of different materials between the elongated structure 1302, 1402 and the bodies 1304, 1404. For instance, at least one of the bodies 1304, 1404 can include a first material while the elongated structure 1302, 1402 can include a second material different than the first material. By way of non-limiting example, the first material can include a polymer, e.g., a molded thermoplastic, while the second material can include a metal, e.g., spring steel. In an embodiment, at least two of the bodies 1304, 1404 installed on the elongated structure 1302, 1402 can have different properties as compared to one another, e.g., the at least two bodies 1304, 1404 can be formed from different materials as compared to one another. In such a manner, the continuum can be designed for use in particular environments where variable continuum attributes, as measured at different locations along the continuum, are desirable.

In an embodiment, the insertion tool 100 can be formed from a first continuum having a single-piece construction and a second continuum having a multi-piece construction. In another embodiment, the insertion tool 100 can be formed from similarly constructed continua, such as two single-piece continua or two multi-piece continua. In yet other embodiments, the insertion tool 100 can be formed from more than two continua, such as three continua, four continua, five continua, and the like.

Insertion tools in accordance with embodiments described herein may generally allow for inspection and operation within a cavity, e.g., of a gas turbine engine, without requiring complex, delicate parts that may break or become stuck within the cavity. Additionally, insertion tools in accordance with embodiments described herein may permit inspection of multiple different areas, e.g., different engines, without use of duplicative tooling specific to each engine design. Yet further, use of insertion tools in accordance with certain embodiments may eliminate longitudinal accuracy requirements between the two or more continua. That is, the continua may be joined together without requiring tight longitudinal tolerances. Moreover, using tools in accordance with certain embodiments described herein can permit infinite adjustability of the curvature and shape of the tool that permit reusability and minimal down time between insertions. This is particularly true for insertion tools which are formed using variable speeds between the first and second continua to permit control of the shape of the insertion tool.

This written description uses examples to disclose the invention, including the best mode, and also to enable any person skilled in the art to practice the invention, including making and using any devices or systems and performing any incorporated methods. The patentable scope of the invention is defined by the claims, and may include other examples that occur to those skilled in the art. Such other examples are intended to be within the scope of the claims if they include structural elements that do not differ from the literal language of the claims, or if they include equivalent structural elements with insubstantial differences from the literal language of the claims.

Further aspects of the invention are provided by the subject matter of the following clauses:

Embodiment 1. A tool system for inserting into a cavity, the tool system comprising: a first continuum having a flexible body defining a first connection interface; and a second continuum having a flexible body defining a second connection interface; and an engagement mechanism configured to couple the first and second connection interfaces of the first and second continua together to form a tool.

Embodiment 2. The tool system of any one or more of the embodiments, wherein the tool has a length defined by a distance between a distal end of the tool configured to be inserted into the cavity and a proximal end of the tool disposed at the engagement mechanism, and wherein at least one of the first and second continua defines a length greater than the length of the tool.

Embodiment 3. The tool system of any one or more of the embodiments, wherein the first and second continua each comprise a body, and wherein the bodies of the first and second continua have the same cross-sectional shapes as one another.

Embodiment 4. The tool system of any one or more of the embodiments, wherein at least one of the first and second continua has a generally C-shaped cross-sectional profile.

Embodiment 5. The tool system of any one or more of the embodiments, wherein the tool system comprises a storage area configured to store portions of at least one of the first and second continua that are not actively part of the tool.

Embodiment 6. The tool system of any one or more of the embodiments, wherein the connection interfaces of the first and second continua comprise at least one of frictional interfaces, electrostatic adhesion interfaces, magnetic interfaces, chemical adhesion interfaces, van der Waal's forces, or any combination thereof.

Embodiment 7. The tool system of any one or more of the embodiments, wherein the engagement mechanism is selected from a plurality of engagement mechanisms, and wherein at least two of the plurality of engagement mechanisms comprises a unique attribute.

Embodiment 8. The tool system of any one or more of the embodiments, wherein radii of curvature of all of the plurality of curved segments are disposed in a same plane.

Embodiment 9. A tool for inserting into a cavity of an aircraft engine, the tool comprising: a flexible first continuum; and a flexible second continuum, wherein the first and second continua are selectively engageable with one another, and wherein when selectively engaged, the first and second continua have a substantially rigid construction.

Embodiment 10. The tool of any one or more of the embodiments, wherein a first half of the tool, as viewed in cross section, comprises the first continuum, and wherein a second half of the tool, as viewed in cross section, comprises the second continuum.

Embodiment 11. The tool of any one or more of the embodiments, wherein the tool comprises a plurality of curved segments when the first and second continua are engaged with one another, wherein each curved segment has a radius of curvature, and wherein all of the radii of curvature are disposed in a same plane.

Embodiment 12. The tool of any one or more of the embodiments, wherein the tool has a length defined by a distance between a distal end of the tool configured to be inserted into the cavity and a proximal end of the tool disposed at an engagement mechanism configured to couple the connection interfaces of the first and second continua together to form the tool, and wherein at least one of the first and second continua defines a length greater than the length of the tool.

Embodiment 13. The tool of any one or more of the embodiments, wherein at least one of the first and second continua comprises a plurality of C-shaped portions coupled together through an elongated structure, and wherein the at least one of the first and second continua are flexible at interfaces disposed between adjacent C-shaped portions.

Embodiment 14. A method of inserting a tool into a cavity, the method comprising: passing a first continuum through an engagement mechanism; passing a second continuum through the engagement mechanism; and coupling the first and second continua together to form the tool using the engagement mechanism, wherein a shape of the formed tool is defined by a shape of the engagement mechanism.

Embodiment 15. The method of any one or more of the embodiments, further comprising selecting the engagement mechanism from a plurality of engagement mechanisms, and wherein at least two of the plurality of engagement mechanisms have different shapes as compared to one another.

Embodiment 16. The method of any one or more of the embodiments, further comprising changing the engagement mechanism from a first engagement mechanism to a second engagement mechanism after passing a first portion of the first and second continua through the first engagement mechanism.

Embodiment 17. The method of any one or more of the embodiments, wherein the formed tool comprises a relatively rigid construction, and wherein the first and second continua each comprise a relatively flexible construction.

Embodiment 18. The method of any one or more of the embodiments, wherein the first and second continua each define a longitudinal length, and wherein coupling the first and second continua together comprises translating at least one of the first and second continua towards the other of the first and second continua in a direction generally transverse to the longitudinal length at a mesh point of the first and second continua.

Embodiment 19. The method of any one or more of the embodiments, further comprising moving a distal end of the tool into the cavity while passing at least one of the first and second continua through the engagement mechanism.

Embodiment 20. The method of any one or more of the embodiments, wherein the first continuum is stored in a rolled configuration, and wherein passing the first continuum through the engagement mechanism is performed by unwinding the first continuum from the rolled configuration.

What is claimed is:

1. A tool system for inserting into a cavity, the tool system comprising:
    a first continuum having a flexible body defining a first connection interface; and
    a second continuum having a flexible body defining a second connection interface; and
    an engager configured to couple the first and second connection interfaces of the first and second continua together to form a tool.

2. The tool system of claim 1, wherein the tool has a length defined by a distance between a distal end of the tool configured to be inserted into the cavity and a proximal end of the tool disposed at the engager, and wherein at least one of the first and second continua defines a length greater than the length of the tool.

3. The tool system of claim 1, wherein the first and second continua each comprise a body, and wherein the bodies of the first and second continua have the same cross-sectional shapes as one another.

4. The tool system of claim 1, wherein at least one of the first and second continua has a generally C-shaped cross-sectional profile.

5. The tool system of claim 1, wherein the tool system comprises a storage area configured to store portions of at least one of the first and second continua that are not actively part of the tool.

6. The tool system of claim 1, wherein 0 an engagement force is applied using a variable shaped actuated section that permits bending of one or more of the first continuum or the second continuum.

7. The tool system of claim 1, wherein the first continuum includes a longitudinal axis and an engagement force applies one or more coupling forces to the first continuum transverse to the longitudinal axis to couple the first continuum with the second continuum.

8. The tool system of claim 1, wherein the first connection interface and the second connection interface of the first and second continua comprise at least one of frictional interfaces, electrostatic adhesion interfaces, magnetic interfaces, chemical adhesion interfaces, van der Waal's forces, or any combination thereof.

9. The tool system of claim 8, wherein the first connection interface and the second connection interface include includes a linear portion extending from one of the first continuum and the second continuum that inserts into a receiver of the other of the first continuum and second continuum.

10. The tool system of claim 1, wherein the engager is selected from a plurality of engagers, and wherein at least two of the plurality of engagers comprises a unique attribute.

11. The tool system of claim 10, wherein radii of curvature of all of a plurality of bent portions of the first continuum and the second continuum are disposed in a same plane.

12. The tool system of claim 1 further comprising a drive machine to move the first continuum and the second continuum.

13. The tool system of claim 12, wherein the drive machine includes an engagement force and is controlled by a controller.

14. The tool system of claim 1, wherein the first continuum and/or the second continuum includes a single, longitudinal extending structure and a plurality of interspaced body portions extending therefrom.

15. The tool system of claim 14, wherein the plurality of interspaced body portions are each separated by a gap, and a size of the gap defines at least in part an amount of bending between the interspaced body portions.

16. A tool for inserting into a cavity of an aircraft engine, the tool comprising:
    a flexible first continuum; and
    a flexible second continuum,
    wherein the first and second continua are selectively engageable with one another, and wherein when selectively engaged, the first and second continua have a substantially rigid construction.

17. The tool of claim 16, wherein a first half of the tool, as viewed in cross section, comprises the first continuum, and wherein a second half of the tool, as viewed in cross section, comprises the second continuum.

18. The tool of claim 16, wherein the tool comprises a plurality of curved segments when the first and second continua are engaged with one another, wherein each curved segment has a radius of curvature, and wherein all of the radii of curvature are disposed in a same plane.

19. The tool of claim 16, wherein the tool has a length defined by a distance between a distal end of the tool configured to be inserted into the cavity and a proximal end of the tool disposed at an engagement mechanism configured to couple the connection interfaces of the first and second continua together to form the tool, and wherein at least one of the first and second continua defines a length greater than the length of the tool.

20. The tool of claim 16, wherein at least one of the first and second continua comprises a plurality of C-shaped portions coupled together through an elongated structure, and wherein the at least one of the first and second continua are flexible at interfaces disposed between adjacent C-shaped portions.

\* \* \* \* \*

UNITED STATES PATENT AND TRADEMARK OFFICE
CERTIFICATE OF CORRECTION

PATENT NO. : 11,977,217 B2
APPLICATION NO. : 17/111650
DATED : May 7, 2024
INVENTOR(S) : Andrew Crispin Graham and Todd William Danko It is certified that error appears in the above-identified patent and that said Letters Patent is hereby corrected as shown below:

In the Claims

In Column 18, Claim 6, Line 12, delete "0 an" and insert -- an --, therefor.

In Column 18, Claim 9, Line 29, delete "includes a" and insert -- a --, therefor.

Signed and Sealed this
Twenty-third Day of July, 2024

Katherine Kelly Vidal
*Director of the United States Patent and Trademark Office*